US006596313B2

(12) United States Patent
Rosenbloom

(10) Patent No.: US 6,596,313 B2
(45) Date of Patent: Jul. 22, 2003

(54) NUTRITIONAL SUPPLEMENT AND METHODS OF USING IT

(75) Inventor: Richard A. Rosenbloom, Elkins Park, PA (US)

(73) Assignee: The Quigley Corporation, Doylestown, PA (US)

( * ) Notice: Subject to any disclaimer, the term of this patent is extended or adjusted under 35 U.S.C. 154(b) by 0 days.

(21) Appl. No.: 10/122,991

(22) Filed: Apr. 15, 2002

(65) Prior Publication Data

US 2003/0099730 A1 May 29, 2003

Related U.S. Application Data

(63) Continuation-in-part of application No. 09/923,090, filed on Aug. 6, 2001.

(51) Int. Cl.$^7$ .............................. A61K 9/20; A61K 35/78
(52) U.S. Cl. ........................ 424/464; 424/439; 424/756
(58) Field of Search ................................. 424/451, 464, 424/440, 489, 455, 441, 439, 756

(56) References Cited

U.S. PATENT DOCUMENTS

| 5,120,538 A | 6/1992 | Oei |
| 5,248,504 A | 9/1993 | Friedman |
| 5,385,734 A | 1/1995 | Friedman |
| 5,401,504 A | 3/1995 | Das et al. |
| 5,494,668 A | 2/1996 | Patwardhan |
| 5,707,630 A | 1/1998 | Morrow |
| 5,861,415 A | 1/1999 | Majeed et al. |
| 6,174,542 B1 | 1/2001 | Hinton et al. |

OTHER PUBLICATIONS

Internet Page; 1001 Herbs For a Healthy Life; Slippery Elm; Copyright 2000; 1001 Herbs; pp. 1 and 2.
Internet Page; Slippery Elm—MotherNature.com Health Encyclopedia; Copyright 1995–2000; MotherNature.com Inc.; pp. 1 and 2.
Internet page; Slippery Elm—facts and information; Symmetry Products with Slippery Elm; Cold Rx; p. 1 of 1; Printed on Apr. 10, 2001.
Internet Page; Unconventional therapies for cancer: 2. Green tea (CMAJ—Apr. 21, 1998); Canadian Medical Association Journal; pp. 1 to 8.
Internet Page; Alternative Therapies: Turmeric; From American Journal of Health–System Pharmacy; 57(12):1121–1122,2000 Kathryn L. Grant, Pharm.D., Assistant Professor College of Pharmacy, Craig D. Schneider, M.D., Fellow, Program in Integrative Medicine College of Medicine, University of Arizona Tucson; Copyright 2000; pp. 1–6.
Internet Page; Alternative Medicine—Horseradish—Herbal Health Products; Copyright 1996; Viable Herbal Solutions; pp. 1 to 3.
Internet Page; Encyclopedia.com; Results for Horse–Radish; pp. 1 and 2; Copyright 2000, Columbia University Press.
Internet Page; National Library of Medicine; PubMed; Cytotoxicity, antioxidant and anti–inflammatory activities of curcumins I–III from Curcuma longa; Ramsewak RS, DeWitt DL, Nair MG; Department of Horticulture and National Food Safety and Toxicology Center, Michigan State University, East Lansing 48824, USA; p. 1; Phytomedicine Jul. 2000; 7(4): 303–8.
Internet Page; National Library of Medicine; PubMed; Anti–Inflammatory studies on Curcuma long (turmeric). Arora, RB, Kapoor V, Basu N, Jain AP; p. 1; Indian J Med Res Aug. 1971; 59(8): 1289–95.
Internet Page; National Library of Medicine; PubMed; Bioactive phytochemicals with emphasis on dietary practices Krishnaswamy K, Raghuramulu, N; National Institute of Nutrition (ICMR), Hyderabad; pp. 1 and 2; Indian J Med Res Nov. 1998; 108: 167–81.
Internet Page; National Library of Medicine; PubMed; Evaluation of anti–inflammatory property of curcumin (diferuloyl methane) in patients with postoperative inflammation; Satoskar RR, Shah SJ, Shenoy SG; p. 1 and 2; Int. J. Clin Pharmacol Ther Toxicol Dec. 1986; 24(12):651–4.
Internet Page; National Library of Medicine; PubMed; Ethnobotany and research on medicinal plants in India; Jain SK; National Botanical Research Institute, Lucknow, India; p. 1 and 2; Ciba Found Symp 1994; 185:153–64; discussion 164–8.

(List continued on next page.)

Primary Examiner—James M. Spear
(74) Attorney, Agent, or Firm—Knoble & Yoshida, LLC

(57) ABSTRACT

A nutritional supplement for promoting the health of salivary glands and supporting the normal or healthy swallowing in a person includes ingredients obtainable from turmeric, ginger, and horseradish. The nutritional supplement may also be used to treat symptoms such as symptoms of a common cold, a sore throat, congestion, mucositis, laryngitis, arthritis, mucous membrane inflammation and sialorrhea is disclosed. This nutritional supplement can be orally administered a person. The nutritional supplement may further include optional ingredients such as ingredients obtainable from slippery elm bark powder and green tea, as well as other optional ingredients. This nutritional supplement may further include a pharmaceutically acceptable carrier for oral administration. A method of promoting the health of salivary glands, supporting the normal or healthy swallowing and/or treating sialorrhea in a person involves administering the nutritional supplement orally to a person one to six times daily, as needed. A method of treating symptoms of a common cold, a sore throat, congestion, laryngitis, mucositis, sialorrhea, arthritis and mucous membrane inflammation involves administering the nutritional supplement of the present invention orally to a patient one to fifteen times daily, as needed. To achieve the best effect, the nutritional supplement should be held in the mouth of a patient for 5 to 60 minutes. A method of administering this nutritional supplement to a carrier carrying viruses to inhibit or exterminate the viruses includes the step of administering the nutritional supplement to the carrier.

18 Claims, No Drawings

OTHER PUBLICATIONS

Internet Page; Curcuma—Turmeric; Alterative Medicine Foundation HerbMed; Plain English summaries of major research articles from Medline abstracts with hyperlink to original.; pp. 1 to 13; Copyright 1998.

Internet Page; Agriculture Research Service; Dr. Duke's Phytochemical and Ethnobotanical Databases; Chemicals and their Biological Activities in: Curcuma longa L. (Zingiberaceae)—Indian Saffron, Turmeric; pp. 1 to 19; Printed on Feb. 27, 2001.

Internet Page; Agriculture Research Service; Dr. Duke's Phytochemical and Teehnobotanical Databases; Chemicals and their Biological Activities in: Armoracia rusticana Gaertn. et al. (Brassicaceae)—Horseradish; pp. 1 to 17; Printed on Feb. 27, 2001.

Internet Page; Agriculture Research Service; Dr. Duke's Phytochemical and Ethnobotanical Databases; Chemicals and their Biological Activies in: Ulmus rubra Muhlenb. (Ulmaceae)—Red Elm, Slippery Elm; pp. 1 to 9; Printed on Feb. 27, 2001.

Internet Page; National Library of Medicine; PubMed; Mechanism of analgesic effect of clonidine in the treatment of dysmenorrhea; Backon J; Mount Pleasant Hospital Addiction Studies Foundation, Lynn, MA; pp. 1 to 2; Med Hypotheses Nov. 1991; 36(3):223–4.

Internet Page; National Library of Medicine; PubMed; Ginger (Zingiber officinale) in rheumatism and musculoskeletal disorders: Srivastava KS, Mustafa T; Department of Environmental Medicine, Odense University, Denmark; pp. 1 to 2; Med Hypotheses Dec. 1992; 39(4): 342–8.

Internet Page; Alternative Medicine Foundation HerbMed; Zingiber—Ginger; Plain English summaries of major research articles from Medline abstracts with hyperlink to original; pp. 1 to 12; Copyright 1998 Alternative Medicine Foundation.

Internet Page; Agricultural Research Service; Dr. Duke's Phytochemical and Ethnobotanical Databases; Ascorbic–Acid; pp. 1 to 4; Printed on Feb. 27, 2001.

Internet Page; Agricultural Research Service; Dr. Duke's Phytochemical and Ethnobotanical Databases; Gentisic–Acid; pp. 1 to 2; Printed on Feb. 27, 2001.

Internet Page; Agriculture Research Service; Dr. Duke's Phytochemical and Ethnobotanical Databases; Kaempferol; pp. 1 to 3; Printed on Feb. 27, 2001.

Internet Page; Agriculture Research Service; Dr. Duke's Phytochemical and Ethnobotanical Databases; Chemicals and their Biological Activities in: Zingiber officinate Roscoe (Zingiberaceae)—Ginger; pp. 1 to 43; Printed on Feb. 27, 2001.

Internet Page; Agriculture Research Service; Dr. Duke's Phytochemical and Ethnobotanical Databases; Biological Activities of Ascorbyl–Palmitate; p. 1; Printed on Feb. 27, 2001.

Internet page; Prinz et al., "Saliva Tannin interactions", *J. Oral Rehabil*, Nov. 2000; 27(11) :991–4.

Internet page; Bacon et al., "Binding affinity of hydrolysable tannins to parotid saliva and to proline–rich proteins derived form it", *J. Agric Food Chem* Mar. 2000; 48(3) : 838–43.

Internet page; Lomniczi et al., "Inhibition of salivary secretion by lipopolysaccharide: possible role of prostaglandins", *Am J. Physiol Endocrinol Metab*m Aug. 2001; 281.

Internet page; Brouet et al., "Curcumin an anti–tumour promoter and anti–inflammatory agent, inhibits induction of nitric oxide synthase in activated macrophages", *Biochem Biophys Res Commun*Jan. 17, 1995; 206.

Internet page, Rettori et al., "Control of salivary secretion by nitric oxide and its role in neuroimmunomodulation", *Ann NY Acad Sci* 2000; 917:258–67.

Internet page, Tjendraputra et al., "Effect of Ginger Constituents and Synthetic Analogues on Cyclooxygenase–2 Enzyme in Intact Cells", *Bioorg Chem* Jun. 2001;29(3):156–163.

Internet article; ALS Survival Guide, Treatment for ALS; Feb. 5, 2002, pp. 1–15; lougehrigsdisease.net/als.

Park, "Sialorrhea,"The Drooling Patient"", Loyola University Health System, The Department of Otolaryngology Head & Neck Surgery, pp. 1–3, luhs.org/depts./otolaryn/P__peds1.htm.

Salzer, "Sialorrhea", Grand Rounds Archive at Baylor, The Bobby r. Alford Department of Otorhinolaryngology and Communicative Sciences, 1–3.

Rettori et al., "Control of Salivary secretion by nitric oxide and its role in neuroimmunomodulation", *Ann NY Acad Sci* 2000;917:258–67.

Mier et al., "Treatmnt of Sialorrhea with glycopyrrolate A Double–blind, Dose–Ranging Study", *Pediatrics & Adolescent Medicine*, vol. 154, No. 12, Dec. 2000.

Internet page, "Where are your salivary glands?",.cfm American Academy of Otolaryngology—Head and Neck Surgery, entnet.org/healthinfo/throat/salivary.

NUTRITIONAL SUPPLEMENT AND METHODS OF USING IT

CROSS-REFERENCE TO RELATED APPLICATIONS

This application is a continuation-in-part of U.S. application Ser. No. 09/923,090 filed on Aug. 6, 2001 and thus claims the benefit of this earlier application under 35 U.S.C. §120.

BACKGROUND OF THE INVENTION

A. Field of the Invention

The present invention relates to a nutritional supplement and methods of using it. More particularly, the present invention relates to a nutritional supplement useful for promoting the health of salivary glands and/or to support normal or healthy swallowing, and to methods for administering the nutritional supplement for at least these purposes.

B. Description of the Prior Art

Treatment of Sialorrhea

Sialorrhea, a symptom related to amyotrophic lateral sclerosis (ALS), and other causes such as achalasia, acoustic neuroma, Bell's palsy, cerebral palsy, cerebrovascular accident (stroke), glossopharyngeal neuralgia, Guillain-Barre syndrome, hypocalcemia, Ludwig's angina, mental retardation, motor-neuron disease, muscular dystrophy, myasthenia gravis, myotonic dystrophy, paralytic poliomyelitis, polymyositis, Parkinson's disease, Radical Cancer surgery, Seventh-nerve palsy, Shy-Drager syndrome, and Wilson's disease, is the excessive drooling due to salivary gland dysfunction such as overproduction of saliva from the salivary glands. Sometimes, sialorrhea may also be induced by drugs such as clonazepam, ethionamide, haloperidol, and transdermal nicotine among others. People have made much effort to treat Sialorrhea. Newall et al reported using beta antagonists to control the excessive secretions of the oral salivary glands and achieve 75% success rates (J. Neurol. Sci., 1996, 139, 43–4). Mier et al have found that ingestion of glycopyrrolate is effective in treating sialorrhea in children. However, 20% of the children being treated with glycopyrrolate experienced substantial adverse effects, enough to require discontinuation of medication (Arch. Pediatr. Adolese. Med., 2000, 154, 1214–1218). Sialorrhea may also be caused by abnormal or unhealthy swallowing by a patient suffering from diseases such as ALS.

According to a recent study by Rettori et al. (Ann. N.Y. Acad. Sci., 2000; 917; 258–67), inhibitors of nitric oxide synthase (NOS) decrease stimulated salivary secretions whereas donors of NOS potentiate stimulated salivary secretions. This indicates that nitric oxide exerts a stimulatory role on salivary secretion.

Treatment of Inflammation

In modem non-herbal medicine, there are two major categories of anti-inflammatory medicines: steroidal and non-steroidal. Steroidal anti-inflammatory medicines are powerful medications, which are based on hormonal substances, such as cortisone. These medications have a stronger anti-inflammatory response than the non-steroidal medicines. They can be taken as pills, injected into the bloodstream, or injected directly into a joint space. There are many non-steroidal anti-inflammatory medications. Acetaminophen, aspirin, ibuprofen, and naproxen are the most common ones.

There are side effects to both of these groups of medicines. They include stomach upset, stomach bleeding or ulcers, kidney problems, hearing problems and ankle swelling. Additionally, the steroidal anti-inflammatory medications can have more serious side effects including: loss of bone mass, cataracts, reduced ability to fight infection, swelling and weight gain, mood changes, high blood pressure, and problems with the bone marrow where blood cells are produced.

Turmeric (*Curcuma longa*)

Turmeric or Haldi in Hindi is used very widely as medicine as well as a common ingredient in Indian cooking. The rhizome of turmeric is used in medicine and food as a fine powder.

The anti-inflammatory effects of curcumin isolated from *Curcuma longa* were reported in Srimal and Dhawan, Pharmacology of Diferuloyl Methane, a Non-steroidal Anti-inflammatory Agent, J. Pharm. Pharmac. 25:447–452 (1973). Significant anti-inflammatory activity comparable with phenylbutazone and hydrocortisone was observed by Arora et al. (Indian Journal of Medical Research 1971, 59, 1289–1291). Curcumin, an alkaloid (diferuloyl methane) isolated from the alcoholic extract of turmeric has been shown to be a potent anti-inflammatory agent and is considered to be its active ingredient. Further work on anti-inflammatory and anti-arthritic activity has also been carried out by Thatte et al (Indian Journal of Pharmacology 1986, 18 (1), 19–21). Turmeric has been found to have significant anti-inflammatory activity both in acute and chronic models. The therapeutic dose for optimal activity if used alone is reported to be in the range of 5 to 10 grams of dry powder daily (Patwardhan, U.S. Pat. No. 5,494,668). This dosage level, however, can produce a feeling of nausea.

Curcumin not only has anti-inflammatory properties but also has anti-oxidant anti-tumor and other valuable properties. When used in low concentrations, curcumin can inhibit nitric oxide synthase (NOS) and, therefore, inhibit nitric oxide production. For example Brouet et al. (Biochem. Biophys. Res. Commmun., Jan. 17, 1995; 206 (2); 533–40) have reported that NOS activity in soluble extracts of macrophages activated for 6–24 hours in the presence of curcumin (10 microM) was significantly lower than that of macrophages activated without curcumin. Northern-blot and immunoblotting analyses demonstrated that significantly reduced levels of the mRNA and 130-kDa protein of inducible NOS were expressed in macrophages activated with curcumin, compared to those with curcumin. Inhibition of NOS induction was maximal when curcumin was added together with lipopolysaccharide (LPS) and interferon-gamma (IFN-gamma) and decreased progressively as the interval between curcumin and LPS/IFN-gamma was increased to 18 hours. Therefore, curcumin, when used in an effective amount, may be used to effectively control overproduction of saliva by virtue of its property of acting as a NOS inhibitor.

Ginger (*Zingiber officinale*)

Native to southern Asia, ginger is a 2- to 4-foot perennial that produces grass-like leaves up to a foot long and almost an inch wide. Ginger root, as it is called in the grocery store, actually consists of the underground stem of the plant, with its bark-like outer covering scraped off.

Chinese medical texts from the fourth century B.C. suggest that ginger is effective in treating nausea, diarrhea, stomachaches, cholera, toothaches, bleeding, and rheumatism. Ginger was later used by Chinese herbalists to treat a variety of respiratory conditions, including coughs and the early stages of colds.

Ginger's modern use dates back to the early 1880s, when a scientist named D. Mowrey noticed that ginger-filled capsules reduced his nausea during an episode of flu. Inspired by this, he performed the first double-blind study of ginger. Germany's Commission E subsequently approved ginger as a treatment for indigestion and motion sickness. Ginger has become widely accepted as a treatment for nausea. Even some conventional medical texts suggest ginger for the treatment of the nausea and vomiting of pregnancy, although others are more cautious.

Ginger gives relief from muscular discomfort and pain. It inhibits prostaglandin and leukotriene biosynthesis and histamine release. Thus it acts as an anti-inflammatory as well as an antacid agent. It is a dual-inhibitor of the lipoxigenase and cycloxigenase system Ginger contains 1–4% essential oil (oleoresin). Used alone fresh Ginger is required to be used in substantially high doses (50 grams daily), which is not only inconvenient but can act as an irritant to the gastric mucosa. In dry form for any significant results 7 to 10 grams of dry ginger powder has to be taken daily. These therapeutic doses of ginger are extremely inconvenient for the patient and affect patient compliance on a daily basis. (See Potwardhan, U.S. Pat. No. 5,494,668.)

Horseradish (*Armoracia rusticana*)

Horseradish, a perennial herb (*Armoracia rusticana*, but sometimes classified in other genera) of the family Cruciferae (mustard family), is native to Central and Southern Europe (where it has long been cultivated in gardens) and naturalized in many parts of North America. It is grown mainly for its roots, which formerly were used medicinally, particularly as an antiscorbutic. Horseradish is also an excellent diuretic, and is good for digestion problems. Herbalists combine horseradish and honey for coughs and asthma treatments. Externally, it is sometimes used to alleviate the pain and stiffness caused by rheumatism.

Friedman, U.S. Pat. No. 5,248,504 and U.S. Pat. No. 5,385,734, has used horseradish to treat nasal and sinus dysfunction. Attempts have also been made to provide oral horseradish remedies for certain ailments. Mays, U.S. Pat. No. 98,875, relates to a medical compound for alleviating and curing asthma, coughs and colds. The compound includes pulverized horseradish. Diets, U.S. Pat. No. 74,205, discloses a medical compound containing horseradish for the cure of consumption.

Slippery Elm (*Ulmus rubra*)

Slippery elm trees are native to North American. Slippery Elm has been employed in traditional herbal medicine for over 100 years. The dried inner portion of the slippery elm bark has been used both by Native Americans and early settlers. Slippery Elm is a nutritious food that was made into a type of pudding for those who had weak stomachs. Slippery Elm is soothing to irritated tissues and has been used in poultices for its ability to encourage healing in wounds. Slippery Elm nourishes the adrenal glands, gastrointestinal tract, and respiratory system. It helps the body expel excess mucus. Other conditions, for which slippery elm is used, include: abscess, broken bones, burns and scalds, cholera, colitis, constipation in children, debility diaper rash, diarrhea in children, diverticulitis, dysentery, hemorrhoids, hiatal hernia, indigestion labor pain, leprosy and sore throat.

Green Tea (*Camellia sinensis*)

Green tea is the dried leaves and leaf buds of the shrub *Camellia Sinensis*. It is mainly produced in China and Japan. Dried tea leaves are composed mainly of phytochemcial known as polyphenols (36%), principally flavonols (including catechins), flavonoids and flavondiol. The leaves also contain plant alkaloids (about 4%), including caffeine, theobromine and theophylline. Much of the research on green tea has been focused on its potential to prevent cancer. Research suggests that the polyphenols in green tea are responsible for its chemopreventive effect (E. Kaegi, Canadian Medical Association Journal, 1998, 158: 1033–35).

It is an object of certain embodiments of the present invention to provide a nutritional supplement to promote the health of salivary glands, and/or to support normal or healthy swallowing.

It is a further object of certain embodiments of the present invention to provide a composition for treating sialorrhea.

It is still a further object of certain embodiments of the present invention to provide a composition for treating some common types of inflammations such as a sore throat, congestion, laryngitis and mucous membrane inflammation.

It is still a further object of certain embodiments of the present invention to provide a method to treat a sore throat, congestion, laryngitis and mucous membrane inflammation by administering a composition made from natural herbs.

It is still a further object of certain embodiments of the present invention to provide a method to treat sialorrhea by administering a composition made from natural herbs.

These and other objects of the present invention will be apparent from the summary and detailed description of the invention, which follow.

SUMMARY OF THE INVENTION

In a first aspect, the present invention relates to a nutritional supplement. The nutritional supplement of the invention may be used for providing nourishment, or, optionally for promoting the health of salivary glands and/or supporting normal or healthy swallowing. The nutritional supplement includes ingredients, which can be obtained from turmeric ginger and horseradish. It has been found that the combination of these ingredients may provide a nutritional supplement that may also be effective in promoting the health of salivary glands and/or supporting normal or healthy swallowing.

In a second aspect, the present invention relates to a method of providing a nutritional supplement that may promote the health of salivary glands and/or support normal or healthy swallowing, by administering an effective amount of the nutritional supplement of the present invention.

In a third aspect, the present invention relates to a method to treat one or more of a common cold, and/or one or more symptoms thereof, a sore throat, congestion, laryngitis, mucositis, mucous membrane inflammation and sialorrhea by orally administering to a patient an effective amount of a composition including ingredients which can be obtained from turmeric, ginger and horseradish, which provides substantial relief from one or more of these symptoms.

In a fourth aspect, the present invention relates to a method of inhibiting the growth of a virus by administering to a carrier carrying the virus a composition including ingredients which can be obtained from turmeric, ginger and horseradish.

In a fifth aspect, the present invention relates to a method of treating one or more symptoms caused by a viral infection by administering a composition including ingredients which can be obtained from turmeric, ginger and horseradish.

In a sixth aspect, the present invention relates to a method of treating inflammation by administering a composition including ingredients which can be obtained from turmeric, ginger and horseradish.

DETAILED DESCRIPTION OF THE PREFERRED EMBODIMENTS

In a first aspect, the present invention relates to a nutritional supplement. The nutritional supplement may be employed for the purpose of providing nourishment. Alternatively, the nutritional supplement of the present may provide some additional benefits such as promoting the health of salivary glands and/or supporting normal or healthy swallowing. The nutritional supplement of the present invention includes ingredients, which can be obtained from turmeric, ginger and horseradish. A novel feature of the present invention is the inclusion of these three ingredients together in one composition.

By "nutritional" or "nutritional supplement" as used herein is meant that the supplements used in the practice of this invention provide a nourishing amount of one or more ingredients derived from turmeric, ginger and horseradish.

As used herein the term "flavors" includes both fruit and botanical flavors.

As used herein the term "sweeteners" includes sugars, for example, glucose, sucrose and fructose. Sugars also include high fructose corn syrup solids, invert sugar, sugar alcohols including sorbitol, and mixtures thereof. Artificial sweeteners are also included within the scope of the term, "sweetener."

As used herein, the term "pharmaceutically acceptable" means a component that is suitable for use with humans and/or animals without undue adverse side effects (such as toxicity, irritation, and allergic responses), commensurate with a reasonable risk benefit ratio. Further, as used herein, the term "safe and effective amount" refers to the quantity of a component, which is sufficient to yield a desired therapeutic response without undue adverse side effects (such as toxicity, irritation, or allergic responses), commensurate with a reasonable risk/benefit ratio when used in the manner described herein.

Each of turmeric, ginger, or horseradish contain active ingredients which may provide some beneficial effect in promoting the health of salivary glands, supporting normal or healthy swallowing, and/or treating one or more symptoms including symptoms of a common cold, a sore throat, congestion, laryngitis, mucositis and mucous membrane inflammation. Turmeric and ginger may further serve as COX-2 inhibitors to treat certain types of inflammation such as that due to arthritis. However, the taste of each of turmeric, ginger, or horseradish at an effective dosage level may be too overpowering for a patient. It has been found that the combination of materials, which can be obtained from turmeric, ginger and horseradish in the nutritional supplement of the present invention provides a substantial beneficial effect, as well as favorable taste characteristics which make the nutritional supplement palatable.

The first ingredient of the nutritional supplement of the present invention may be obtained from turmeric. The yellow pigment of the rhizome of turmeric is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane) (see Drug Analysis by Chromatography and Microscopy, p. 169, Ann Arbor Science Inc., 1973). The essential oils of turmeric (*curcuma longa*) are primarily composed of the following compounds: d-Camphor (1%), Cyclo-isoprenemyrcene (85%), and p-Tolylmethylcarbinol (5%), (see E. Gunther, The Essential Oil, p. 123–4, Van Nostrand Co., 1955).

The first ingredient, obtained from turmeric, preferably includes curcuminoids, such as curcumin (diferuloylmethane), desmethoxycurcumin (hydroxycinnamoyl feruloylmethane), and bis-desmethoxycurcumin (dihydroxydicinnamoyl methane), and mixtures of two or more of these curcuminoids.

Methods for isolating curcuninoids from turmeric are known, (see Janaki and Bose, An Improved Method for the Isolation of Curcumin From Turmeric, J. Indian Chem. Soc. 44:985 (1967)). Alternatively, curcuminoids for use in the present invention can be prepared by synthetic methods.

The first ingredient, which can be obtained from of turmeric can be incorporated into the nutritional supplement of the present invention in a variety of different forms. Those different forms preferably include extracts of turmeric such as turmeric powder extracts, turmeric fluid extracts, one or more the curcuminoid compounds, and turmeric powder parts of or whole plants of turmeric; tinctures thereof; and mixtures thereof. More preferably, the first ingredient is a turmeric extract.

The second ingredient of the nutritional supplement of the present invention may be obtained from ginger (also commonly called ginger root). Non-steroidal anti-inflammatory drugs have three major actions, all of which are related to inhibition of cyclo-oxygenase resulting in decreased formation of prostanoids. Firstly, an anti-inflammatory action achieved by reduced production of vasodilator prostaglandins (PGE2, PGI2), which means less vasodilation and, indirectly less oedema. Secondly, an analgesic effect achieved by reduced prostaglandin production (less sensitization of nociceptive nerve endings to the inflammatory mediators bradykinin and 5-hydroxytryptamine). Thirdly, an antipyretic effect which is probably due to a decrease in the mediator PGE2 generated in response to inflammatory pyrogens, much as interleukin-1. Ginger inhibits prostanoid synthesis and also products of 5-lipoxygenase. The potency of the ginger extract in the acute inflammation test appears to be comparable to that exhibited by acetyl salicylic acid reported in the same study. (Mascolo N. et al Journal of Ethnopharmocology 1989, 27, 129–140).

One of the features of inflammation is increased oxygenation of arachidonic acid, which is metabolized by two enzymic pathways—the cyclooxygenase (CO) and the 5-lipoxygenase (5-LO)-leading to the production of prostaglandins and leukotrienes respectively. It is suggested (Srivastava and Mustafa; Medical Hypotheses; 1992; 39 342–348) that at least one of the mechanisms by which ginger shows its ameliorative effects could be related to inhibition of prostaglandin and leukotriene biosynthesis, i.e. it works as a dual inhibitor of eicosanoid biosynthesis.

Ginger contains 1–4% essential oil (oleoresin). Many chemical investigations have been carried out on the constituents of the essential oil of ginger. All together more than 200 different volatiles have been identified in the essential oil of ginger. The essential oil of ginger contains a mixture of various terpenes as well as some other non-terpenoid compounds.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linolenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γaminobutyric acid, γ-terpineine, geranial, geraniol, geranylacetate, gingerenone, glutamic acid, glycine, hexahydrocurcumin, histidine, isogingerenone-B, isoleucine kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

The second ingredient of the nutritional supplement of the present invention, which may be obtained from ginger, can be incorporated in the nutritional supplement of the present invention in many different forms including ginger extracts such as ginger powder extracts, ginger fluid extracts, ginger powder, and one or more active compounds of ginger; parts of or whole ginger plants; tinctures thereof; and mixtures thereof. Also, for any specific active compound of ginger for which suitable synthesis routes are known, the active compound can be prepared synthetically. Preferably, the second ingredient of the nutritional supplement of the present invention is selected from ginger extract, and ginger root powder.

A third ingredient of the nutritional supplement of the present invention may be obtained from horseradish (also commonly called horseradish root). Horseradish's pharmacological activities are mainly due to its active compounds. The active compounds of horseradish which may be useful in the present invention include, but are not limited to, allyl-isothiocyanate, amylase, arginine, ascorbic acid, asparagine, gentisic acid, kaempferol, limonene, niacin, p-hydroxy-benzoic acid, pectin, phenylpropyl-isothiocyanate, quercetin, raphanin, riboflavin, rutoside, selenium, sinapic acid, sinigrin, tannin, thiamin, vanillic acid and zinc, as well as mixtures of two or more of these compounds.

The third ingredient of the nutritional supplement of the present invention, which may be obtained from horseradish, can be included in the nutritional supplement in many different forms. Those different forms include horseradish powder, horseradish extracts such as horseradish powder extracts and horseradish fluid extracts, and one or more active compounds of horseradish; parts of or whole plants of horseradish; tinctures thereof; and mixtures thereof. For a particular active compound, for which a synthetic route is known, the active compound may be obtained synthetically. Preferably, the third ingredient of the nutritional supplement of the present invention is selected from horseradish powder and horseradish extract.

All active compounds of the present invention may be obtained from other sources, if available. Thus, the phrase "which can be obtained from" or the phrase "which may be obtained from" is meant to encompass compounds or nutritional supplements that are obtainable from turmeric, ginger, horseradish, slippery elm or green tea and therefore encompasses synthetic forms of the same compounds and/or compositions as well as the same compounds and/or compositions obtained from other sources.

The ingredients of the nutritional supplement of the present invention, which may be obtained from turmeric, ginger and horseradish, may be used in the forms of turmeric powder, ginger powder, horseradish powder which may be ground from the rhizome of turmeric, ginger root and horseradish root respectively. Alternatively, turmeric powder, ginger powder, horseradish powder, and/or one or more of the active compounds contained therein may be purchased from commercial sources such as Delavau Co. Alternatively, the ingredients of the present invention can be used in the form of turmeric extract, ginger extract and horseradish extract, which may be extracted from each of turmeric rhizome, ginger root and horseradish roots using common extraction procedures. One suitable extraction procedure is described below.

The extraction procedure comprises, generally, the steps of:

1) cleaning the plant from which the pharmacologically or biologically active plant extract has to be obtained to remove any foreign matter thereon;

2) particulating the plant to obtain a particulate mass having particle size ranging from 0.001 to about 10 mm$^3$; and 3) subjecting the particulate mass to at least one polar and at least one non-polar solvent to obtain separate fractions of the plant extract soluble in the respective solvents, and mixing the fraction so obtained to obtain the beneficiated plant extract in accordance with this invention.

For instance, in the case of turmeric, the process comprises the steps of:

1) cleaning the roots of turmeric to remove any foreign matter thereon;

2) particulating the roots to obtain a particulate mass having particle size ranging from 0.001 to about 10 mm$^3$;

3) subjecting the particulate mass to distillation to obtain a volatile fraction, if any, from the particulate mass;

4) cooking the distilled particulate mass in a polar solvent, such as water to soluble material in the distillation-treated particulate.mass to obtain a first solution and a first residue;

5) filtering the first solution from the first residue;

6) evaporating the filtrate obtained from the first solution to remove the solvent and obtain a solute designated as fraction A from the particulated mass;

7) subjecting the first residue to treatment with a second polar solvent such as 75% to 95% ethanol for twelve to thirty-six hours to obtain a second solution and a second residue;

8) filtering the second solution from the second residue to obtain a second filtrate;

9) evaporating the second filtrate to remove its solvent and obtain a solute designated as fraction B from the particulated mass;

10) subjecting the second residue to less polar or non-polar solvents; such as petroleum ether, for twelve to thirty-six hours to obtain a third solution and a third residue, and filtering the third solution from the third residue to obtain a third filtrate;

11) evaporating the third filtrate to remove its solvent and obtain a solute designated as fraction C from the particulated mass; and 12) homogeneously mixing the volatile fraction, with fractions A, B and C from the particulated mass to obtain a beneficiated plant extract.

The process is suitable for the preparation of a pharmacologically or biologically active plant extracts substantially in a convenient administrable dosage form from any of the plants mentioned above.

Solvents useful for extracting turmeric include water, ethanol, propanol, paraffin, hexane, petroleum ether, toluene, acetone, methyl ethyl ketone, and other common organic solvents. Water, ethanol and petroleum ether are the preferred solvents for extracting turmeric. Solvents useful for extracting ginger include water, ethanol, propahol, paraffin, petroleum ether, hexane, toluene, acetone, methyl ethyl ketone, and other common organic solvents. Ethanol, water and acetone are the preferred solvents for extracting ginger. Solvents useful for the extracting horseradish include water, ethanol, propanol, paraffin, petroleum ether, hexane, toluene, acetone, methyl ethyl ketone, and other common organic solvents. Water and ethanol are the preferred solvents for extracting horseradish.

Most preferably, the nutritional supplement of the present invention includes turmeric extract, ginger root powder and horseradish root powder in a safe and effective amount to provide one or more of the beneficial effects described herein.

Each gram of the nutritional supplement of the present invention preferably contains 5 mg to 20 mg of turmeric extract. Most preferably, each gram of the nutritional supplement contains 7 mg to 15 mg of turmeric extract.

Each gram of the nutritional supplement of the present invention preferably contains 30 mg to 150 mg of ginger root powder. Most preferably, each gram of the nutritional supplement contains 50 mg to 110 mg of ginger root powder.

Each gram of the nutritional supplement of the present invention preferably contains 25 mg to 70 mg of horseradish root powder. Most preferably, each gram of the nutritional supplement contains 40 mg to 60 mg of horseradish root powder.

Preferably, the nutritional supplement of the present invention may further include a fourth ingredient, namely a suitable demulcent, which may soothe and mobilize mucous membrane in the mouth of a patient. The demulcent may be obtained from slippery elm. Alternatively, the demulcent may be selected from pectin, mucilage and carageenan.

The active compounds of slippery elm, which may be useful in the present invention include, but are not limited to, ascorbic acid, β-carotene, β-sitosterol, citrostadienol, magnesium, manganese, mucilage, niacin, riboflavin, selenium, tannin, thiamin, zinc and mixtures thereof.

Preferably, the fourth ingredient of the nutritional supplement of the present invention, which may be obtained from slippery elm, is incorporated into the nutritional supplement of the present invention in a form selected from slippery elm bark powder, slippery elm extracts such as slippery elm powder extracts, slippery elm fluid extracts, and one or more active compounds of slippery elm; slippery elm bark; tinctures thereof; and mixtures thereof. Slippery elm bark powder may be produced by grinding slippery elm bark. Slippery elm extract may be produced by extracting from slippery elm bark using well-known extraction processes. For a particular active compound, for which a synthetic route is known, the active compound may be synthesized. Alternatively, the slippery elm bark powder, the slippery elm extract and/or the active compounds of slippery elm may be purchased from commercial sources such as Delavau Co.

Preferably, the fourth ingredient of the nutritional supplement of the present invention is selected from slippery elm extract and slippery elm bark powder. More preferably, the fourth ingredient of the nutritional supplement is slippery elm bark powder. Each gram of the nutritional supplement of the present invention preferably contains 50 mg to 150 mg of slippery elm bark powder. Most preferably, each gram of the nutritional supplement contains 75 mg to 120 mg of slippery elm bark powder.

Preferably, the nutritional supplement of the present invention may further include a fifth ingredient, which may be obtained from green tea. The fifth ingredient obtained from green tea may have an antioxidant effect.

The pharmacological activities of green tea are mainly due to its active compounds. The active compounds of green tea useful in the present invention include, but are not limited to, flavonols, catechins, flavonoids, flavondiols, plant alkaloids, caffeine, theobromine, theophylline, phenolic acids, proteins, carbohydrates, and minerals.

The fifth ingredient of the nutritional supplement of the present invention, which may be obtained from green tea, can be included in the nutritional supplement in the form of green tea powder, green tea extracts such as green tea powder extracts, green tea fluid extracts, and one or more active compounds of green tea; part of or whole green tea plants; green tea leaves; tinctures thereof; or mixtures thereof. The green tea powder can be produced by grinding dry green tea leaves. The green tea extract may be produced by extracting from dry green tea leaves using the common extraction methods. For a particular active compound of green tea, for which a synthetic route is known, the active compound may be synthesized. Alternatively, the green tea powder, the green tea extract and/or the active compounds of green tea can be purchased from commercial sources such as Delavau Co.

Preferably, the fifth ingredient of the nutritional supplement of the present invention is selected from green tea leaves, green tea-powder and green tea extract. More preferably, the fifth ingredient of the nutritional supplement of the present invention, which may be obtained from green tea, is green tea extract. Each gram of the nutritional supplement of the present invention preferably contains 5 mg to 20 mg of green tea extract. Most preferably, each gram of the nutritional supplement contains 7 mg to 15 mg of green tea extract.

The nutritional supplement of the present invention may be used for the provision of nutrition by simply ingesting the nutritional supplement, as needed, to provide a nutritional benefit. The nutritional supplement of the present invention may also be employed to promote the health of salivary glands and/or supporting normal or healthy swallowing. By promoting the health of salivary glands, and/or supporting normal or healthy swallowing, the nutritional supplement of the present invention may be useful in improving the quality of life of a person suffering from, for example, sialorrhea.

The nutritional supplement of the present invention may also be used as a therapeutic composition to treat one or more of a common cold and/or one or more symptoms thereof, a sore throat, congestion, laryngitis, mucositis, and/or mucous membrane inflammation by oral administration to a patient suffering from one or more of these symptoms or ailments. The nutritional supplement of the present invention may also be used to treat sialorrhea caused, for example, by ALS. The nutritional supplement of the present invention may also be used to treat inflammation such as that due to arthritis, based at least in part on the COX-inhibition properties of some of its ingredients such as components obtainable from ginger, turmeric and green tea. The nutritional supplement of the present invention may further be used to treat viral infection, and inflammation such as that caused by arthritis. In addition, the nutritional supplement of the present invention has significant virucidal and virustatic properties as demonstrated by some the following examples.

In a preferred embodiment, the nutritional supplement of the present invention may further include other natural COX-2 inhibitors such as ingredients obtained from one or more of Chinese goldthread and barberry, holy basil, baikal skullcap, Hu zhang (Japanese Knotweed), rosemary, oregano, feverfew and hops. The additional ingredients which may exhibit COX-2 inhibiting properties include, but are not limited to, one or more of apigenin, baicalein, berberine, catechins, curcumin, eicosapentaenoic-acid, eugenol, evodiame, evodol, humulone, kaemperol, oleanolic acid, parthenolide, resveratrol, rutaecarpine, salicylic acid, trans-reveratrol and ursolic acid. These additional ingredients can be incorporated in the nutritional supplement of the present invention in the form of a powder, apart of or a whole plant, a powder extract, a fluid extract, a tincture, when applicable, and mixtures thereof.

The nutritional supplement of the present invention may be formulated using a safe and effective amount of the three main ingredients discussed above to provide one or more of the beneficial effects of the invention described herein, and one or more of the optional ingredients which may be obtained from slippery elm or green tea, as well as one or more of the additional optional ingredients described below. The nutritional supplement of the present invention may also be formulated with a pharmaceutically acceptable carrier.

Preferably, the nutritional supplement of the present invention may be formulated in any orally acceptable dosage forms including, but not limited to, capsules, tablets, lozenges, troches, hard candies, powders, sprays, gels, elixirs, syrups, and suspensions or solutions.

The pharmaceutically acceptable carrier may include, but is not limited to: (a) carbohydrates including sweeteners, more preferably, fructose, sucrose, sugar, dextrose, starch, lactose, maltose, maltodextrins, corn syrup solids, honey solids, commercial tablet nutritional supplements including Emdex.RTM., Mor-Rex.RTM., Royal-T.RTM., Di-Pac.RTM., Sugar-Tab.RTM., Sweet-Rex.RTM., New-Tab.RTM., (b) sugar alcohols including mannitol, sorbitol, xylitol, and (c) various relatively insoluble excipients including dicalcium phosphate, calcium sulfate, calcium carbonate, microcrystalline cellulose and other pharmaceutical tableting ingredients.

Lozenges, tablets and troches in this invention are essentially the same, but may differ in shape, size and manufacturing technique.

In the case of tablets, for oral use, the pharmaceutically acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenge's for oral use, the common pharmaceutically acceptable carrier may further include a binder such as PEG-8000. Preferably lozenges are made in a 0.1 to 15 grams size to allow a suitable dissolution rate for lozenges. More preferably lozenges are made in an 1 to 6 gram size to allow a suitable dissolution rate for lozenges. Dissolution time should be about 15 minutes in water bath testers at 37° C. degrees or about 30 minutes when orally dissolved as lozenges for promoting the health of salivary glands, supporting normal or healthy swallowing, and/or treating a sore throat, congestion, laryngitis, sialorrhea, and mucous membrane inflammation.

To directly make compressible lozenges, add the active ingredients to PEG-8000 processed fructose; or add the active ingredient of the nutritional supplement to crystalline fructose and commercially available, sweet, direct compression products such as Mendell's Sugartab.RTM., Sweetrex.RTM., or Emdex.RTM. Add saccharin if desired, flavors as desired, glidants such as silica gel as needed, and lubricants such as magnesium stearate as needed. The mixture should be kept dry and tableted soon after mixing. The ingredients are mixed and directly compressed into lozenges using conventional pharmaceutical mixing and tableting equipment. The compressive force is preferably sufficient to produce maximum hardness throughout the lozenges to preserve the dissolution rate and maximize the efficacy of lozenges. Dissolution should occur over a sustained period of time, that being 5 to 60 minutes, and preferably about 20 to 30 minutes. The nutritional supplement should be stored in an airtight container and in a cool dark place.

Tablets and troches can be manufactured using procedures similar to that described above with minor changes in the optional ingredients.

Alternatively, the nutritional supplement of the present invention may be formulated in liquid form, such as syrups, mouthwashes or sprays with a solvent or dispersant such as water, or other liquids in a pharmaceutically acceptable carrier for repeated delivery of the nutritional supplement to oral and oropharyngeal mucous membranes over a sustained period of time. Preferably, the treatment time is about 5 to 60 minutes, and more preferably about 20 to 30 minutes, so as to permit a prolonged contact of the nutritional supplement with mouth and throat tissues. Alternatively, such formulations can be in a form suitable for dilution with water or other materials prior to use.

The nutritional supplement may also be formulated in chewable nutritional supplements such as soft candy, gum drops, liquid filled candies, chewing gum bases and dental supplies, such as toothpastes and mouthwashes by further including fructose, sucrose, or saccharin in the nutritional supplement, as needed. In use, the chewable composition is retained in the mouth over a sustained period of time of preferably about 5 to 60 minutes, and more preferably about 20 to 30 minutes.

The nutritional supplement of the invention may be formulated in capsule form with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The nutritional supplement of the present invention may also be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons and/or other conventional solubilizing or dispersion agents.

Other materials, which may optionally be included in the nutritional supplement of the present invention include inositol, other B-complex vitamins, and anti-inflammatories. Also, ingredients such as sweeteners, flavorants, coloring agents, dyes, preservatives, emulsifying agents, suspending agents, melting agents, excipients, and solvents or diluents such as water, ethanol, propylene glycol, glycerin and various combinations thereof, may be included in the nutritional supplement of the present invention.

The optional sweeteners which may be used in the nutritional supplement of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the nutritional supplement.

The optional flavorants which may be used in the nutritional supplement of the present invention-include, but are not limited to, peppermint, peppermint-menthol, eucalyptol wintergreen, licorice, clove, cinnamon, spearmint, cherry, lemon, orange lime, menthol and various combinations thereof.

Preferably, the three main ingredients described above which may be derived from turmeric, ginger and horseradish, make up from about 0.5–90% by weight of the total composition of the nutritional supplement. More preferably, the three main ingredients will make up 10–70% by weight of the total composition. Most preferably, the three main ingredients make up 20–40% by weight of the total composition.

The non-carrier ingredients of the nutritional supplement, including the ingredients obtainable from turmeric, ginger, horseradish, slippery elm, and green tea as discussed above, can be increased or decreased proportionally in the nutritional supplement of the present invention depending on the amount of carrier used in the nutritional supplement without substantially affecting the effectiveness of the nutritional supplement for its intended use.

In another aspect, the present invention relates to a method of promoting the health of salivary glands and/or supporting normal or healthy swallowing by administering an effective amount of the nutritional supplement of the present invention.

The nutritional supplement may be administered 1–6 times per day, as needed, more preferably, 1–2 times per day, as needed, or most preferably, 6–10 times per day, as needed. As discussed above, the nutritional supplement of the present invention may be administered to a person in any orally acceptable dosage form including, but not limited to tablets, capsules, lozenges, troches, hard candies, powders, sprays, gels, elixirs, syrups, and suspensions or solutions.

Preferably, during each administration of the nutritional supplement, the nutritional supplement in a lozenge form is held in the mouth of the person for at least 5 to 60 minutes to enable the main ingredients of the nutritional supplement to contact the mouth tissue or throat before it completely dissolves. More preferably, the nutritional supplement is held in the mouth of the person for at least 15 to 30 minutes. Preferably, an effective amount of the nutritional supplement for each administration contains 0.1 gram to 1 gram of the three main ingredients, which may be obtained from turmeric, ginger and horseradish. More preferably, an effective amount of the nutritional supplement for each administration contains 0.2 gram to 0.5 gram of the three main ingredients.

In a third aspect, the present invention relates to a method of administering to a patient an amount of the nutritional supplement of the present invention, which is effective to provide substantial relief of one or more symptoms of a common cold, as well as one or more of a sore throat, congestion, laryngitis, mucositis, mucous membrane inflammation sialorrhea. In this method, the nutritional supplement of the present invention is used as a therapeutic composition.

The effective amount of the nutritional supplement will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the nutritional supplement, and the severity of the illness or symptom. It is within the skill of the person of ordinary skill in the art to account for these factors.

The method of the present invention involves the administration of a composition of the present invention to a patient that suffers from one or more of a common cold, a sore throat, congestion, laryngitis, mucositis, sialorrhea and mucous membrane inflammation. The effective amount of the nutritional supplement will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the nutritional supplement, and the severity of the illness or symptom. It is within the skill of the person of ordinary skill in the art to account for these factors.

The nutritional supplement may be administered 1–15 times per day, as needed, more preferably, 2–12 times per day, as needed, or most preferably, 6–10 times per day, as needed. As discussed above, the nutritional supplement of the present invention may be administered to a patient in any orally acceptable dosage form including, but not limited to tablets, capsules, lozenges, troches, hard candies, powders, sprays, gels, elixirs, syrups, and suspensions or solutions.

The method of the present invention initially treats acute symptoms but may be continued indefinitely to provide substantial relief of one or more, a common cold, a sore throat, congestion, laryngitis, mucositis, sialorrhea, and mucous membrane inflammation, to prevent the symptoms of a common cold, sore throat, congestion, laryngitis and mucous membrane inflammation from returning and possibly cure one or more of these symptoms or ailments.

Preferably, during each administration of the nutritional supplement, the nutritional supplement is held in the mouth of the patient for at least 5 to 60 minutes to enable the main ingredients of the nutritional supplement to contact the mouth tissue or throat before it completely dissolves. More preferably, the nutritional supplement is held in the mouth of the patient for at least 15 to 30 minutes. Preferably, an effective amount of the nutritional supplement for each administration contains 0.1 gram to 1 gram of the three main ingredients, which may be obtained from turmeric, ginger and horseradish. More preferably, an effective amount of the nutritional supplement for each administration contains 0.2 gram to 0.5 gram of the three main ingredients.

For treatment of sialorrhea, significantly less frequent dosages of the nutritional supplement may be sufficient to provide effective relief. Preferably, 1–6 doses per day are used for sialorrhea. More preferably, only 1–2 doses per day are employed to treat sialorrhea.

In a fourth aspect, the present invention relates to a method of inhibiting the growth of a virus and/or exterminating a virus by administered to a carrier carrying the virus a nutritional supplement including ingredients which can be obtained from turmeric, ginger and horseradish. In this method, the nutritional supplement of the present invention is used as an antiviral agent and may have one or both of a virustatic effect and a virucidal effect.

In the method, the virus that may be inhibited by the antiviral agent of the present invention includes, among other viruses, at least rhinoviruses. In a preferred embodiment, the virus that may be inhibited by the antiviral agent includes human rhinoviruses.

In the method, the carrier may be a human, an in vitro cell or an animal. Preferably, the carrier is a human.

The antiviral agent may be administered 1–15 times per day, as needed, more preferably, 2–12 times per day, as needed, or most preferably, 6–10 times per day, as needed. As discussed above, the antiviral agent of the present invention may be administered to a human in any orally acceptable dosage form including, but not limited to tablets, capsules, lozenges, troches, hard candies, powders, sprays, gels, elixirs, syrups, and suspensions or solutions.

Preferably, during each administration of the antiviral agent a lozenge of the composition is held in the mouth of a human for at least 5 to 60 minutes to enable the main ingredients of the antiviral agent to contact the mouth tissue or throat before it completely dissolves. More preferably, the antiviral agent is held in the mouth of the human for at least 15 to 30 minutes.

In a fifth aspect, the present invention relates to a method of treating a viral infection, or one or more symptoms caused by a viral infection in a person by administering a composition including ingredients which obtained from turmeric, ginger and horseradish as an antiviral agent to the person.

The symptoms caused by a viral infection which may be treated by this method of the present invention, may include one or more of head ache, joint pain, fever, cough, sneezing, muscle ache, running nose, dry mouth, dizziness, and other symptoms related to viral infection. The viral infection may be caused by rhinoviruses including human rhinoviruses.

The antiviral agent may be administered 1–15 times per day, as needed, more preferably, 2–12 times per day, as needed, or most preferably, 6–16 times per day, as needed. As discussed above, the antiviral agent of the present invention may be administered to a person in any orally acceptable dosage form including, but not limited to tablets, capsules, lozenges, troches, hard candies, powders, sprays, gels, elixirs, syrups, and suspensions or solutions.

Preferably, during each administration of the antiviral agent, a lozenge of the antiviral agent is held in the mouth of a person for at least 5 to 60 minutes to enable the main ingredients of the antiviral agent to contact the mouth tissue or throat before it completely dissolves. More preferably, the antiviral agent is held in the mouth of the person for at least 15 to 30 minutes.

In another aspect, the present invention relates to a method of treating one or more symptoms of inflammation, which may be caused by, for example, arthritis, by administering a composition including ingredients, which can be obtained from turmeric, ginger and horseradish as a therapeutic composition to the person. The symptoms may include one or more of joint pain, joint immobility, joint stiffness and other symptoms related to arthritis.

It has been found that the therapeutic composition of the present invention has analgesic properties due to its COX-2 inhibiting and anti-inflammatory properties. The therapeutic composition of the present invention can be used to relieve the pain or other symptoms caused by human arthritis or similar afflictions. To relieve the symptoms of arthritis, the therapeutic composition may be administered 1–15 times per day, as needed, more preferably, 2–12 times per day, as needed, or most preferably, 6–10 times per day, as needed. As discussed above, the therapeutic composition of the present invention may be administered to a person in any orally acceptable dosage form including, but not limited to tablets, capsules, lozenges, troches, hard candies, powders, sprays, gels, elixirs, syrups, and suspensions or solutions.

Preferably, during each administration of the therapeutic composition, a lozenge of the therapeutic composition is held in the mouth of a person for at least 5 to 60 minutes to enable the main ingredients of the therapeutic composition to contact the mouth tissue or throat before it completely dissolves. More preferably, the therapeutic composition is held in the mouth of the person for at least 15 to 30 minutes.

The invention will be further illustrated by the examples given below which are not to be construed as limiting the invention in any way.

EXAMPLES

Example 1

A Nutritional Supplement of the Present Invention

A nutritional supplement of the present invention formulated in the form of lozenges was prepared using the procedure described above. The ingredients of the lozenge are listed below:

| | |
|---|---|
| Sugar | 1 g |
| Slippery elm bark | 118 mg |
| Turmeric extract (5% curcumin) | 18 mg |
| Ginger root | 140 mg |
| Horseradish root | 70 mg |
| Green tea leaf extract (30% catechin and polyphenols) | 14 mg |

Example 2

Treatment of Sore Throat

Each of seven patients, suffering from sore throats, ingested one lozenge of Example 1 every two hours by holding the lozenge in his or her mouth for about 15–30 minutes until the lozenge completely dissolves. No patient took more than 10 lozenges in any given day.

The patients, that were treated, reported complete relief from the symptoms of their sore throats after ingesting from 2 to 20 lozenges. It was also found that each lozenge can provide relief from a sore throat for up to 6 hours.

Example 3

Treatment of Sialorrhea

Two patients, who suffer from sialorrhea caused by ALS, ingested 1–2 lozenges of example 1 every day for a three-week period. It was found that the ingestion of the lozenges effectively controlled excessive secretions of saliva in these two patients. In both patients, excessive drooling was also significantly reduced.

Example 4

In Vitro Testing of Virucidal Activity of the Nutritional Supplement

The in vitro testing protocol for virucidal activity uses human rhinovirus 16 (hereafter "HRV-16") as the target virus, uses the MRC-5 cell line related to human tissues described by Jacobs, et al, *Characteristics of Human diploid MRC-5*, Nature (Lond), 227, p168–170 (1970) as the host cell for the HRV-16 viruses. Residual virus infectivity following incubation of the test substances with the virus is titrated on the MRC-5 cell line for rhinovirus growth by visually scoring the cytopathic effect (CPE) induced by virus replication through microscopic observation. More specifically, CPE is generally scored by observing ballooning/rounded cells in the MRC-5 culture.

To determine the virucidal activity, the nutritional supplement composition of Example 1 (hereafter "Substance 1"), at an initial dilution of 1/20 and then further serial dilutions in saline, were incubated with HRV-16 for a set time.period and then the reaction was terminated to a neutral pH with cell infection media. The terminated solution was then titrated out on MRC-5 cells at a dilution of 1/10 across a testing plate to carry out the infection of the cells. Each plate housed a virus control, which contains only HRV-16 infected MRC-5 cells, and a cell control, which contains only uninfected MRC-cells.

The plates were further incubated for 4 days after the infection. Residual viral infectivity is measured using the assay discussed above. From the results shown in Tables 1–4, all the controls on the plate worked well.

From the assay, it was concluded that Substance 1 at a 1/20 dilution was effective in producing a HRV-16 viral log reduction of 1.50 (−log 10 TCID50) at the 1-minute incubation period. A 1/40 dilution of Substance 1 produced a log reduction of 1.00 (−log 10 TCID50) also at the 1-minute incubation period. After the 2-minute and 5-minute, incubation periods, 1/2 a log reduction in HRV-16 titre were achieved. Therefore, the 1-minute contact time of Substance 1 with HRV-16 would produce the most effective viral titre reduction.

Table 1 shows the residual virus titres and log reduction of infectious Rhinovirus 16 on MRC-5 cells after 1 termination time point of Substance 1 at different dilutions.

TABLE 1

| Dilutions | pH value of Substance 1 in Isotonic solution | pH value of terminated solution | 1 Minute Incubation | | |
|---|---|---|---|---|---|
| | | | Virus Control (TCID50) | Residual Virus titre (TCID50) | Log Reductions (TCID50) |
| 1/20 | 5.03 | 7.73 | 3.80 | 2.30 | 1.50 |
| 1/40 | 5.13 | 7.77 | 3.80 | 3.30 | 0.50 |
| 1/80 | 4.98 | 7.83 | 3.80 | 3.80 | 0.00 |
| 1/160 | 4.98 | 7.73 | 3.80 | 3.80 | 0.00 |

Tables 2–4 show a second trial on the residual virus titres and log reduction of infectious HRV-16 on MRC-5 cells at 3 termination time points of Substance 1 different dilutions.

TABLE 2

| | | 1 Minute Incubation | |
|---|---|---|---|
| Dilutions of Substance 1 | HRV-16 Control Titre (TCID50) | Residual HRV-16 titre (TCID50) | HRV-16 log Reductions (TCID50) |
| 1/20 | 3.30 | 1.80 | 1.50 |
| 1/40 | 3.30 | 2.30 | 1.00 |
| 1/80 | 3.30 | 2.80 | 0.50 |
| 1/160 | 3.30 | 2.80 | 0.50 |
| 1/320 | 3.30 | 2.80 | 0.50 |

TABLE 3

| | | 2 Minute Incubation | |
|---|---|---|---|
| Dilutions of Substance 1 | HRV-16 Control Titre (TCID50) | Residual HRV-16 titre (TCID50) | HRV-16 log Reductions (TCID50) |
| 1/20 | 3.30 | 2.80 | 0.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |

TABLE 4

| | | 5 Minute Incubation | |
|---|---|---|---|
| Dilutions of Substance 1 | HRV-16 Control Titre (TCID50) | Residual HRV-16 titre (TCID50) | HRV-16 log Reductions (TCID50) |
| 1/20 | 3.30 | 2.80 | 0.50 |
| 1/40 | 3.30 | 2.80 | 0.50 |
| 1/80 | 3.30 | 3.30 | 0.00 |
| 1/160 | 3.30 | 2.80 | 0.50 |
| 1/320 | 3.30 | 2.80 | 0.50 |

In Tables 1–4, TCID50=−log 10 TCID50.

Example 5

In Vitro Testing of Virustatic Activity of the Nutritional Supplement

The in vitro testing protocol for virucidal activity used human rhinovirus 16 (HRV-16) as the target virus, and the rhinovirus sensitive Hela cell line related to human tissues described by Conant et al, *Basis for a numbering system. I. Hela cells for propagation and serologic procedure,* J. Immunol., 100, p107–113 (1968) as the host cell for the HRV-16 viruses.

The nutritional supplement of Example 1, Substance 1, was dissolved in infection media to the following dilutions: 1/20, 1/40, 1/80, 1/160 and 1/320. These dilutions were incubated on plates of MRC-5 cells for 30 minutes at 37 C (5% CO2). After the incubation period, each Substance 1 dilution with MRC-5 cells in a well of the plates was subjected to HRV-16 at a known titre of 2.30 (−log 10 TCID50). Each plate housed a virus control (the Hela cells infected with HRV-16 viruses and without Substance 1), a cell control (Hela cells only) and the test compound controls at the different dilutions (Hela cells with the test substance only). All the other samples on the plate contained the Hela cells infected with HRV-16 viruses and Substance 1 at different dilutions. The plates were further incubated for 4 days after infection.

Residual virus infectivity following incubation of Substance 1 with the virus was titrated on the Hela cell line for rhinovirus growth by measuring the cytopathic effect (CPE) induced by the viruses using the following procedure.

The remaining viable Hela cells after incubation with Substance 1 were stained with crystal violet solution. Excess crystal violet was removed by washing and the crystal violet stained cells were solubilized using a mixture of methanol and acetic acid. The absorbance of the solution was then measured at 540 nm in an ELISA plate reader. The level of virus induced CPE was inversely proportional to the absorbance.

The results generated from the Crystal violet assay enabled the toxic concentration and the effective concentration of Substance 1 to be determined by fitting an equation, y=mx+c, wherein x corresponds to the dilution of Substance 1 and y corresponds to percentage of toxicity of Substance 1 to the cells. From this equation, the TC50 (concentration at which Substance 1 indicates 50% toxicity to the cells) is at a 1/571 dilution of Substance 1.

This result correlates well with the percentage of cell survivors at various dilution of Substance 1, which was also measured using the crystal violet assay, as shown in Table 5 below.

TABLE 5

| Dilution of Substance 1 without Virus | % Cell Survivors |
|---|---|
| 1/320 | 89.7 |
| 1/160 | 94.6 |
| 1/80 | 97.6 |
| 1/40 | 109.3 |
| 1/20 | 168.2 |

Using the same equation, wherein x still corresponds to the dilution of Substance 1 and y corresponds to the percent efficacy of Substance 1 in the presence of the virus, the EC50 (concentration at which the test substance indicates 50% efficacy in the presence of virus) was determined to be at a 1/91 dilution of Substance 1. This result correlates well with the percentage of viable cells at various dilutions of Substance 1 measured using the crystal violet assay, as shown in Table 6 below.

TABLE 6

| Substance 1 dilution and Virus | % Viable Cells |
|---|---|
| 1/320 + HRV-16 | 79.3 |
| 1/160 + HRV-16 | 62.3 |
| 1/80 + HRV-16 | 39.0 |
| 1/40 + HRV-16 | 15.9 |
| 1/20 + HRV-16 | −220.0 |

In Tables 5 and 6, "% Cell Survivors"=("Compound only"/"Cell only")×100; and "% Viable Cells"=("Cell only"−"Compound+Virus")/("Cells only"−"virus only")×100.

"Compound only" denotes the measurement results for the wells containing only Hela cells and Substance 1 at a predetermined dilution.

"Cell only" denotes the measurement results for the wells containing only uninfected Hela cells.

"Compound+Virus" denotes the measurement results for the wells containing both the Hela cells infected with HRV-16 viruses and Substance 1 at a predetermined dilution. "Virus Only" denotes the measurement results for the wells containing the Hela cells infected with HRV-16 only.

Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto.

I claim:

1. A method for providing nourishment comprising the step of administering a safe and effective amount of a nutritional supplement to a human or animal, to provide a nourishing amount of each ingredient of the nutritional supplement, said nutritional supplement comprising a first ingredient obtainable from turmeric;
   a second ingredient obtainable from ginger; and
   a third ingredient obtainable from horseradish.

2. A method as claimed in claim 1, wherein the nutritional supplement further comprises:
   a fourth ingredient obtainable from slippery elm; and
   a fifth ingredient obtainable from green tea.

3. A method as claimed in claim 1, wherein the step of administering the nutritional supplement comprises the step of retaining the nutritional supplement in the mouth for a period of from about 5 to about 60 minutes.

4. A method as claimed in claim 3, wherein the step of retaining the nutritional supplement in the mouth is carried out for a period of from about 15 to about 30 minutes.

5. A method as claimed in claim 1, wherein the step of administering the nutritional supplement to the person is carried out 1 to 6 times per day.

6. A method as claimed in claim 5, wherein the step of administering the nutritional supplement is carried out 1 to 2 times per day.

7. A method for promoting health of salivary glands and/or supporting normal or healthy swallowing comprising the step of administering, to a human or animal, a safe and effective amount of a nutritional supplement comprising a first ingredient obtainable from turmeric;
   a second ingredient obtainable from ginger; and
   a third ingredient obtainable from horseradish.

8. A method as claimed in claim 7, wherein the nutritional supplement further comprises:
   a fourth ingredient obtainable from slippery elm; and
   a fifth ingredient obtainable from green tea.

9. A method as claimed in claim 7, wherein the step of administering the nutritional supplement comprises the step of retaining the nutritional supplement in the mouth for a period of from about 5 to about 60 minutes.

10. A method as claimed in claim 9, wherein the step of retaining the nutritional supplement in the mouth is carried out for a period of from about 15 to about 30 minutes.

11. A method as claimed in claim 7, wherein the step of administering the nutritional supplement to the person is carried out 1 to 6 times per day.

12. A method as claimed in claim 11, wherein the step of administering the nutritional supplement is carried out 1 to 2 times per day.

13. A method for treating one or more symptoms selected from the group consisting of symptoms of a common cold, mucositis, sialorrhea, a sore throat, congestion, laryngitis and mucous membrane inflammation comprising the step of administering to a patient an effective amount of a composition, said composition comprising:
   a first ingredient obtainable from turmeric;
   a second ingredient obtainable from ginger; and
   a third ingredient obtainable from horseradish.

14. A method as claimed in claim 13, wherein the composition further comprises:
   a fourth ingredient obtainable from slippery elm; and
   a fifth ingredient obtainable from green tea.

15. A method as claimed in claim 13, wherein the step of administering the composition to a patient comprises the step of retaining the composition in the mouth of the patient for a period of from about 5 to about 60 minutes.

16. A method as claimed in claim 15, wherein the step of retaining the composition in the mouth of the patient is carried out for a period of from about 15 to about 30 minutes.

17. A method as claimed in claim 15, wherein the step of administering the composition to a patient is carried out 1 to 15 times per day.

18. A method as claimed in claim 17, wherein the step of administering the composition to a patient is carried out 2 to 10 times per day.

* * * * *